(12) United States Patent
Hautaviita et al.

(10) Patent No.: US 10,737,027 B2
(45) Date of Patent: Aug. 11, 2020

(54) MEDICAMENT DELIVERY DEVICE

(71) Applicant: CAREBAY EUROPE LTD, Sliema (MT)

(72) Inventors: Nikolaj Hautaviita, Bro (SE); Stefan Gylleby, Stockholm (SE); Per Lindstedt, Värndö (SE); Daniel Säll, Segeltorp (SE); Rasmus Renstad, Stockholm (SE)

(73) Assignee: SHL MEDICAL AG, Zug (CH)

( * ) Notice: Subject to any disclaimer, the term of this patent is extended or adjusted under 35 U.S.C. 154(b) by 251 days.

(21) Appl. No.: 15/544,081

(22) PCT Filed: Jan. 25, 2016

(86) PCT No.: PCT/EP2016/051447
§ 371 (c)(1),
(2) Date: Jul. 17, 2017

(87) PCT Pub. No.: WO2016/120207
PCT Pub. Date: Aug. 4, 2016

(65) Prior Publication Data
US 2018/0008773 A1    Jan. 11, 2018

(30) Foreign Application Priority Data

Jan. 27, 2015 (SE) ..................................... 1550083

(51) Int. Cl.
*A61M 5/20*       (2006.01)
*A61M 15/00*     (2006.01)

(52) U.S. Cl.
CPC ...... *A61M 5/2033* (2013.01); *A61M 15/0081* (2014.02); *A61M 2005/2013* (2013.01);
(Continued)

(58) Field of Classification Search
CPC .. A61M 15/0081; A61M 5/2033; A61M 5/20; A61M 5/3157; A61M 2205/276;
(Continued)

(56) References Cited

U.S. PATENT DOCUMENTS 7,449,012 B2 * 11/2008 Young ................. A61M 5/3245
604/192
2007/0179448 A1    8/2007 Lim et al.
(Continued)

FOREIGN PATENT DOCUMENTS

CN        1799071 A       7/2006
CN      101166551 A       4/2008
(Continued)

OTHER PUBLICATIONS

International Search Report and Written Opinion for Int. App. No. PCT/EP2016/051447, completed Apr. 28, 2016.
Chinese Office Action for CN Application No. 2016800006978.6 dated Mar. 16, 2020.
Chinese Office Action for CN App. No. 201680006978.6, dated May 25, 2020.

*Primary Examiner* — Bhisma Mehta
*Assistant Examiner* — Nidah M Hussain
(74) *Attorney, Agent, or Firm* — McDonnell Boehnen Hulbert & Berghoff LLP

(57) ABSTRACT

A medicament delivery device is presented having a housing that is arranged to accommodate a medicament container; a drive unit operably arranged to act on the medicament container upon activation; an activation mechanism operably arranged to be operated by a user; an activation preventing mechanism operably arranged to prevent said activation mechanism to be activated; an identification module arranged to be operated by a user, which identification module is designed as an attachable unit to the medicament delivery device; mechanical keying elements arranged on said device and on said identification module designed to interact with each other when attaching said identification (Continued)

module; first electrical keying elements comprised in said identification module, wherein said electrical keying elements are capable of obtaining identification information, such that the identification information obtained is compared to stored data and authenticated by the identification module, and wherein the authentication causes a deactivation of the activation preventing mechanism to allow operation of the activation mechanism.

19 Claims, 12 Drawing Sheets

(52) U.S. Cl.
CPC .............. *A61M 2005/2073* (2013.01); *A61M 2205/276* (2013.01); *A61M 2205/3368* (2013.01); *A61M 2205/3553* (2013.01); *A61M 2205/3569* (2013.01); *A61M 2205/3592* (2013.01); *A61M 2205/52* (2013.01); *A61M 2205/6009* (2013.01); *A61M 2205/6027* (2013.01); *A61M 2205/6045* (2013.01); *A61M 2205/6054* (2013.01); *A61M 2205/6063* (2013.01)

(58) Field of Classification Search
CPC .. A61M 2205/3553; A61M 2205/6027; A61M 2205/6045; A61M 2205/6054; A61M 2205/6063; A61M 2205/6009; A61M 2205/3569; A61M 2205/52; A61M 2005/3247; A61M 2005/2073; A61M 2005/208; A61M 2205/6033
See application file for complete search history.

(56) References Cited

U.S. PATENT DOCUMENTS

| | | | |
|---|---|---|---|
| 2007/0186923 A1* | 8/2007 | Poutiatine | A61M 15/0083 128/200.14 |
| 2007/0225653 A1 | 9/2007 | Lim et al. | |
| 2009/0294521 A1* | 12/2009 | de la Huerga | A61J 1/035 235/375 |
| 2013/0204202 A1* | 8/2013 | Trombly | A61M 5/172 604/207 |
| 2013/0324934 A1 | 12/2013 | Holmqvist et al. | |
| 2014/0194817 A1 | 7/2014 | Lee et al. | |
| 2014/0357304 A1* | 12/2014 | Ostrander | H04W 4/023 455/456.3 |
| 2017/0197025 A1* | 7/2017 | Adams | A61M 5/142 |
| 2017/0258994 A1* | 9/2017 | Schiendzielorz | A61M 5/172 |

FOREIGN PATENT DOCUMENTS

| | | |
|---|---|---|
| CN | 101495080 A | 7/2009 |
| CN | 103442756 A | 12/2013 |
| CN | 104147664 A | 11/2014 |
| JP | 2006524069 A | 10/2006 |
| JP | 2009526553 A | 7/2009 |
| WO | 2004/095379 A1 | 11/2004 |
| WO | 2007/041843 A1 | 4/2007 |
| WO | 2007/081947 A2 | 7/2007 |
| WO | 2008/085764 A1 | 7/2008 |
| WO | 2012/080481 A1 | 6/2012 |
| WO | 2013/048310 A1 | 4/2013 |
| WO | 2013/178512 A1 | 12/2013 |

* cited by examiner

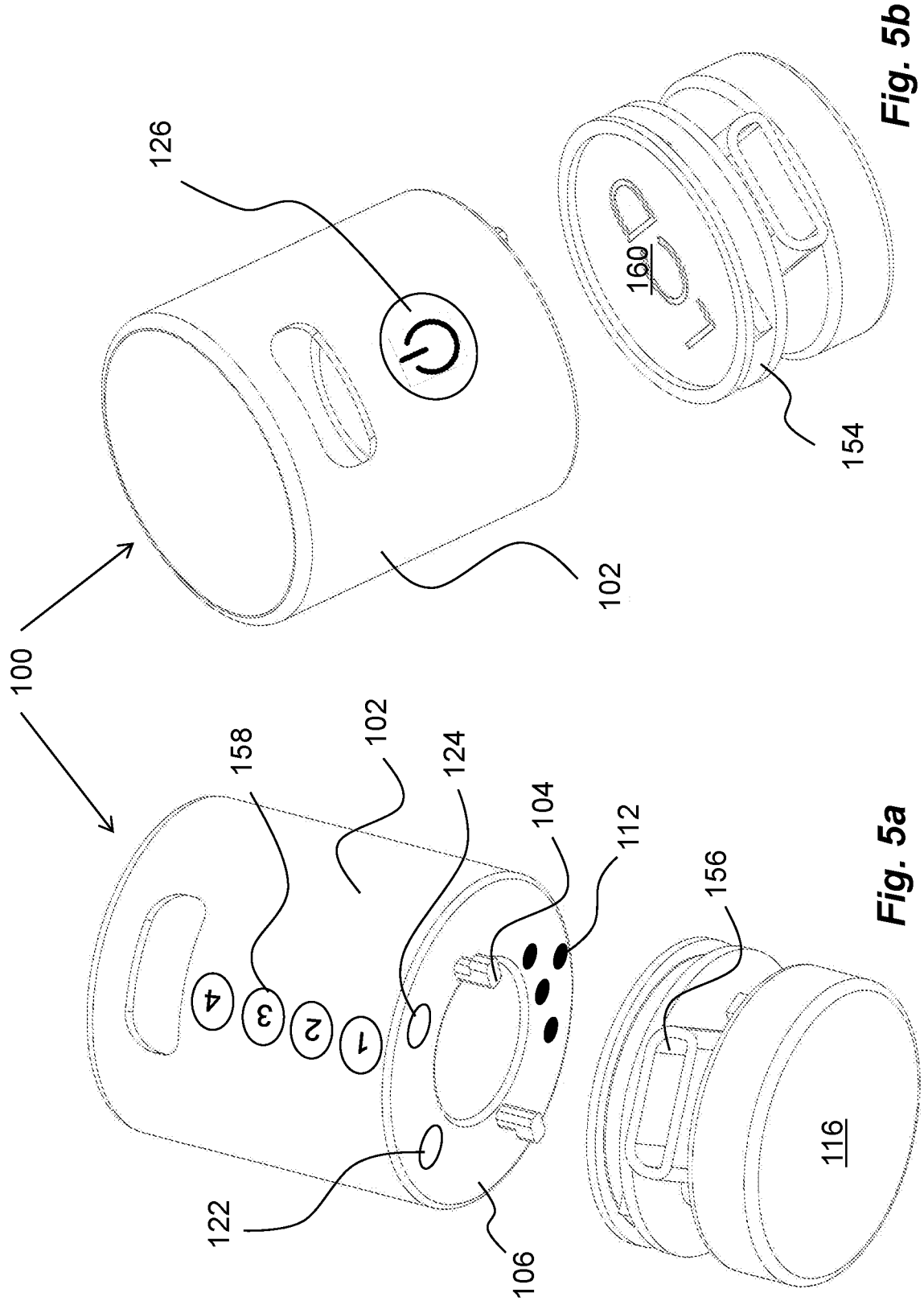

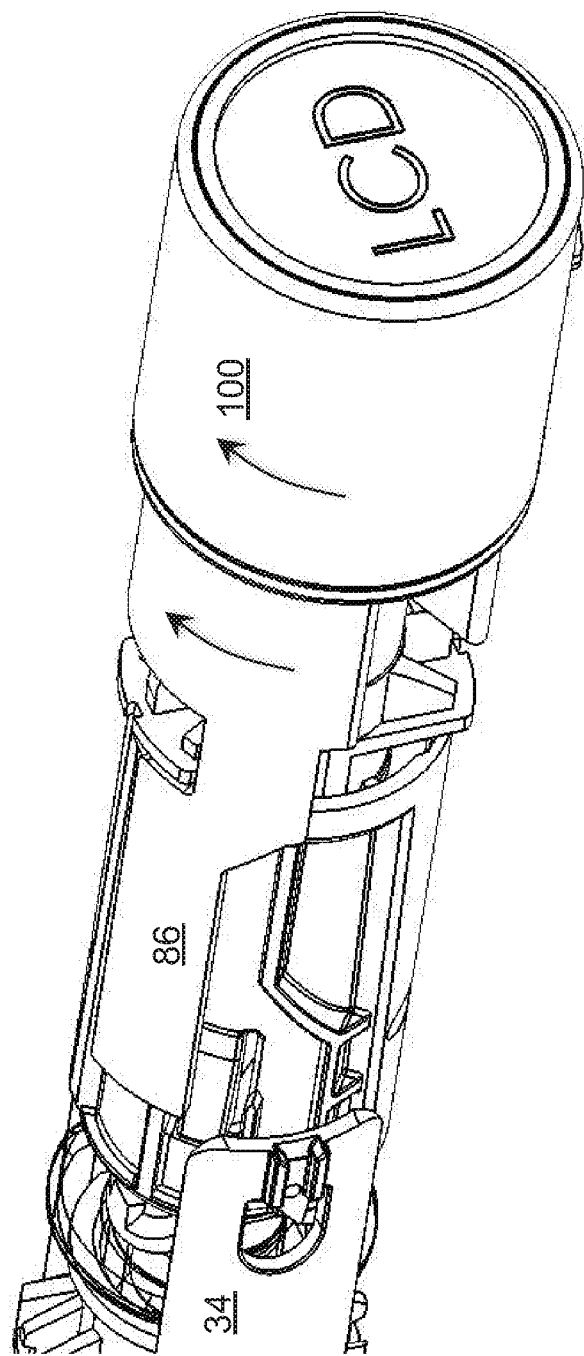

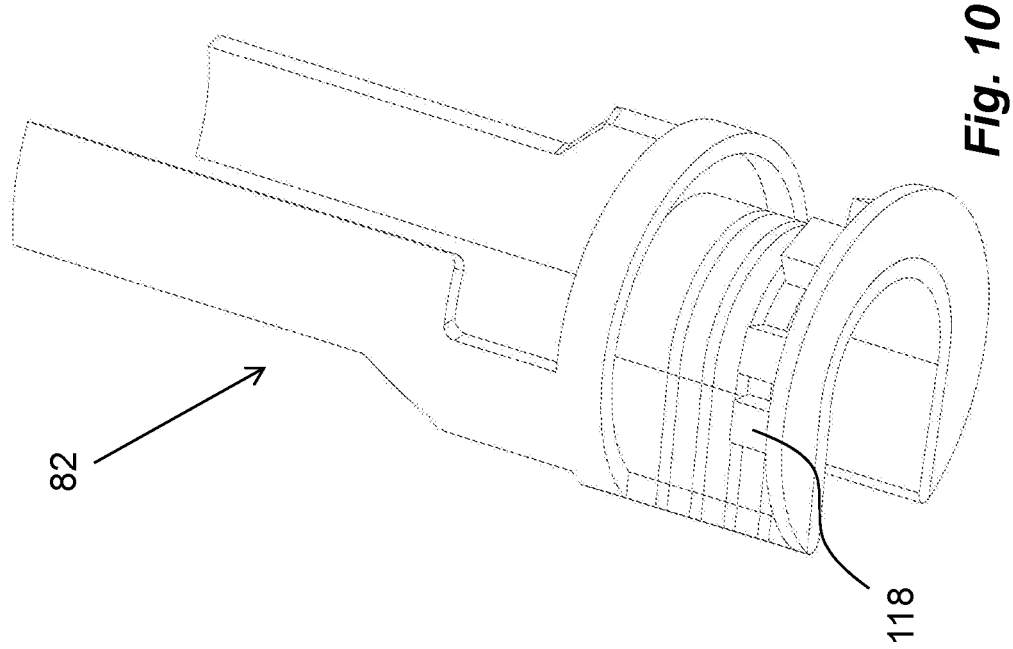
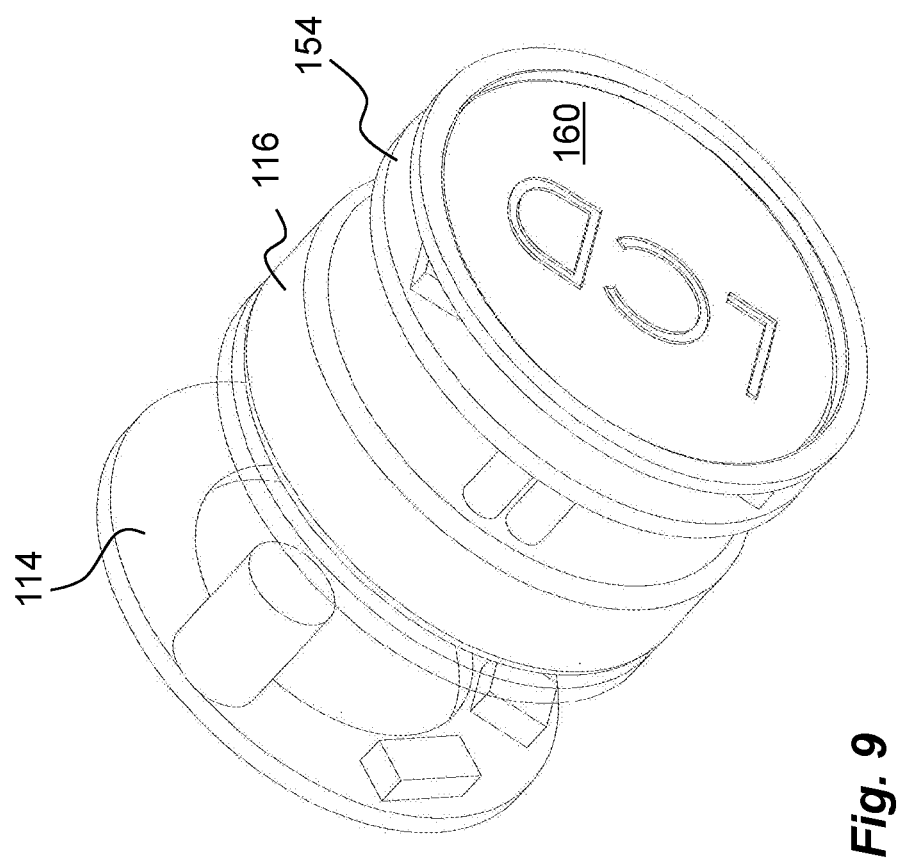

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/051447 filed Jan. 25, 2016, which claims priority to Swedish Patent Application No. 1550083-8 filed Jan. 27, 2015. The entire disclosure contents of these applications are herewith incorporated by reference into the present application.

TECHNICAL AREA

The present disclosure relates to medicament delivery devices and in particular medicament delivery devices provided with mechanisms related to specific approved users.

BACKGROUND

The number of medicament delivery devices that are intended to be handled by the persons that are prescribed the drug or other persons helping the person that has the prescribed drug. The latter may be e.g. parents helping their children to administer the drug, or elderly people having home care personnel.

As many of the drugs that are administered are quite expensive, such as for example hormone therapies, and as the treatment often is heavily subsidised by many countries, there is a pronounced risk that the receivers of the drugs are tempted to sell them to others that cannot get hold of the drugs legally and that are willing to pay a lot of money.

Another risk, especially when the drug is expensive, is that a person unintendedly activates the medicament delivery device and fires off and thus wastes a dose or even several doses. This is also a problem if the drug is vital to a patient and where it may be lethal of the patient does not receive a dose according to treatment scheme, or also during an emergency situation.

A few attempts have been made to secure a medicament delivery device from being handled by non-authorised or non-approved persons, but so far the solutions presented have a number of drawbacks and/or can be manipulated in order to "override" the safety aspects.

BRIEF DESCRIPTION OF INVENTION

The aim of the present disclosure is to remedy the drawbacks of the state of the art medicament delivery devices in this area. This aim is obtained by a medicament delivery device having the features of the independent patent claims. Preferable embodiments are found in the dependent patent claims.

The medicament delivery device as described herein may comprise a housing, which housing is arranged to accommodate a medicament container. The medicament container may be arranged with a suitable medicament delivery member that is capable of delivering a dose to a user. The medicament delivery member may be an injection needle, a mouth or nose piece or a nebulizer for inhaling the drug, etc. in order to deliver a dose, a drive unit may be operably arranged to act on the medicament container upon activation.

Further an activation mechanism may be operably arranged to be operated by a user, as well as an activation preventing mechanism operably arranged to prevent said activation mechanism to be activated. Thereby the activation preventing mechanism will not permit the delivery of a dose until certain criteria are met.

According to a preferable solution, an identification module may be arranged to be operated by a user. The identification module may be designed to be unique to a specific medicament delivery device, such that, when the identification module is operated and is identified by the specific medicament delivery device as unique, the activation preventing mechanism will be deactivated to allow operation of the activation mechanism.

This enables a solution for preventing the use of the medicament delivery device unless the user has an identification module that fits with the medicament delivery device. Only then can the medicament delivery device be activated and a dose be delivered. This solution greatly reduces the risk of e.g. unintentional activation and possible wasting of medicament that may be very expensive and/or vital. Further, there is a much reduced risk that the user will be tempted to sell the medicament delivery device, and certainly with the additional features that will be described below.

According to one feasible solution, the identification module may be designed as an attachable unit to the medicament delivery device. With this feature, the same identification module may be used for several medicament delivery devices. This is a pronounced advantage if the medicament delivery devices are so called disposables. The user may then receive a number of medicament delivery devices having the same unique features that function with the one unique identification module. When one medicament delivery device has been used, the identification module may be removed, the used medicament delivery device discarded and the identification module attached to another medicament delivery device.

According to one solution, the unique design of the identification module may comprise unique mechanical keying elements designed and arranged to interact with corresponding unique keying elements of the medicament delivery device. In this aspect, the mechanical keying elements may preferably be arranged with unique patterns, number, shapes and sizes. Thereby, the keying elements are "customized" in that many different combinations may be obtained.

The activation preventing mechanism may be a blocking element and that the deactivation by the identification module will cause the blocking element to be moved to a non-blocking position. The blocking element then blocks any or several components of the medicament delivery device that may be used for activate the delivering of a dose.

As an alternative, the unique design of the identification module may comprise unique electrical keying elements designed and arranged to interact with corresponding unique keying elements of the medicament delivery device. In that respect, the electrical keying elements may be arranged with unique electrical information transferable between the identification module and the medicament delivery device. Also with this alternative, the activation preventing mechanism may be a blocking element.

With the electrical alternative there is a possibility that the deactivation may be performed by electrical power, magnetic fields or, heat generated by the identification module. The power, magnetic field and/or the heat may cause a number of different actions that will affect the blocking element.

In order to further increase the safety and identification aspects, the identification module may comprise electrical input elements for identifying an approved user. The input elements could comprise buttons for providing a unique code and/or biometrical sensors. With this solution it is very difficult to activate the medicament delivery device if you are not the approved user that for example has been given a unique code to be entered via the buttons. Even higher security is obtained with biometrical sensor that could read fingerprints, eyes, faces of persons. With that scenario, the selling aspect is greatly reduced.

According to a further preferable solution, the identification module may comprise communication circuits. These circuits may be arranged to communicate with communication elements in the medicament delivery device and/or with external communication elements. For instance, the medicament delivery device may be arranged with sensors and circuits internally that are capable of sensing different states and conditions of the medicament delivery device and its components. Further, if the identification module is arranged to communication externally, then it may be able to transmit information and data from the medicament delivery device as well as obtaining information and data from external sources. This transmitted information and data could be used to further strengthen the identification process of specific users.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

In the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form, eye dispensers, crème/gel dispensers, etc. The medicament delivery devices may be of either disposable type or re-usable type and may be provided with medicament containers suitably arranged for specific drugs in specific forms.

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the interne, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with short range wireless communication technologies like e.g. RFID, NFC or Bluetooth. The smart devices are also arranged with programs capable of establishing and handling the communication with RFID tags, NFC tags or Bluetooth circuits.

Further, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

Figure 1:
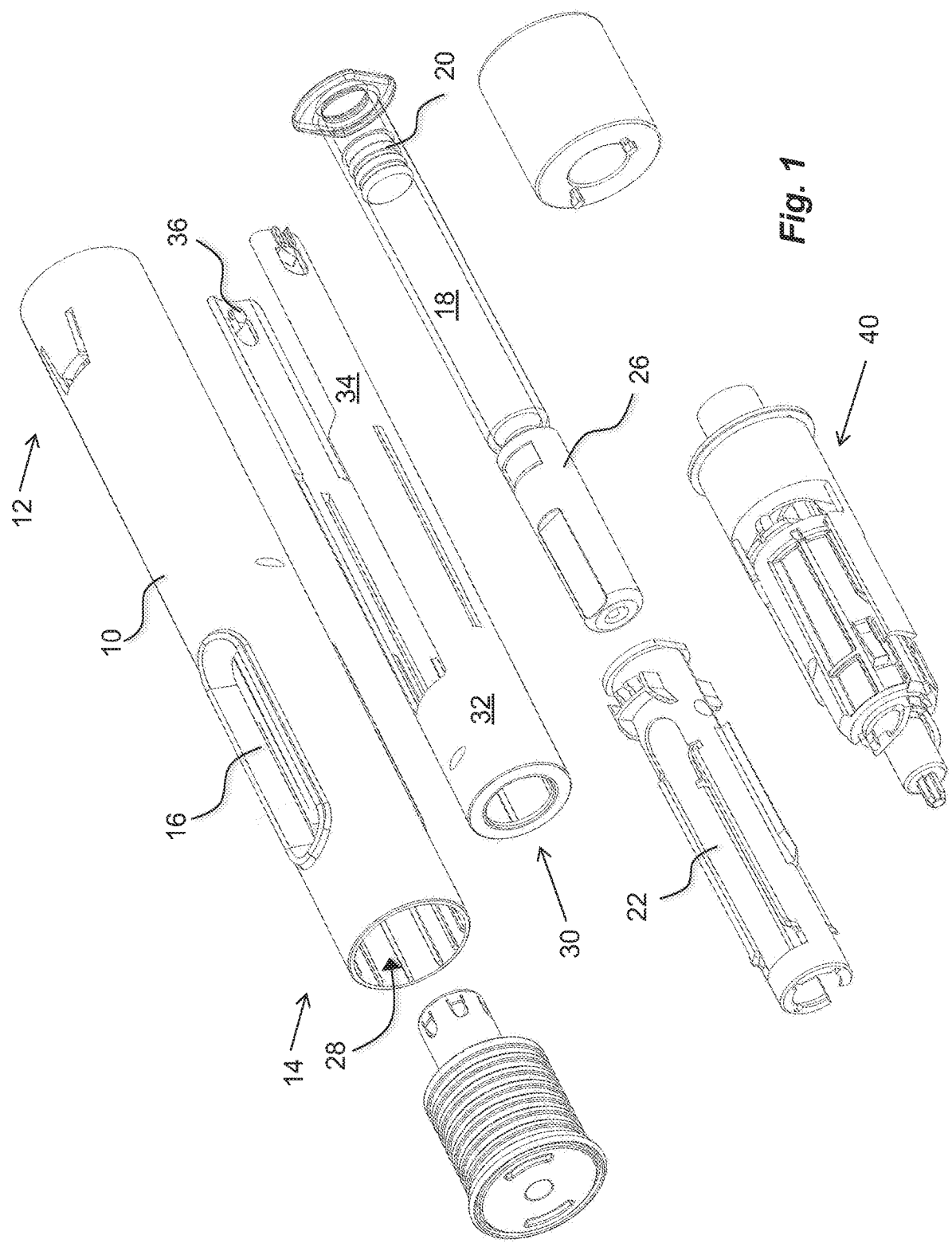
FIG. 1 is an exploded view of one embodiment of a medicament delivery device.
Figure 2:
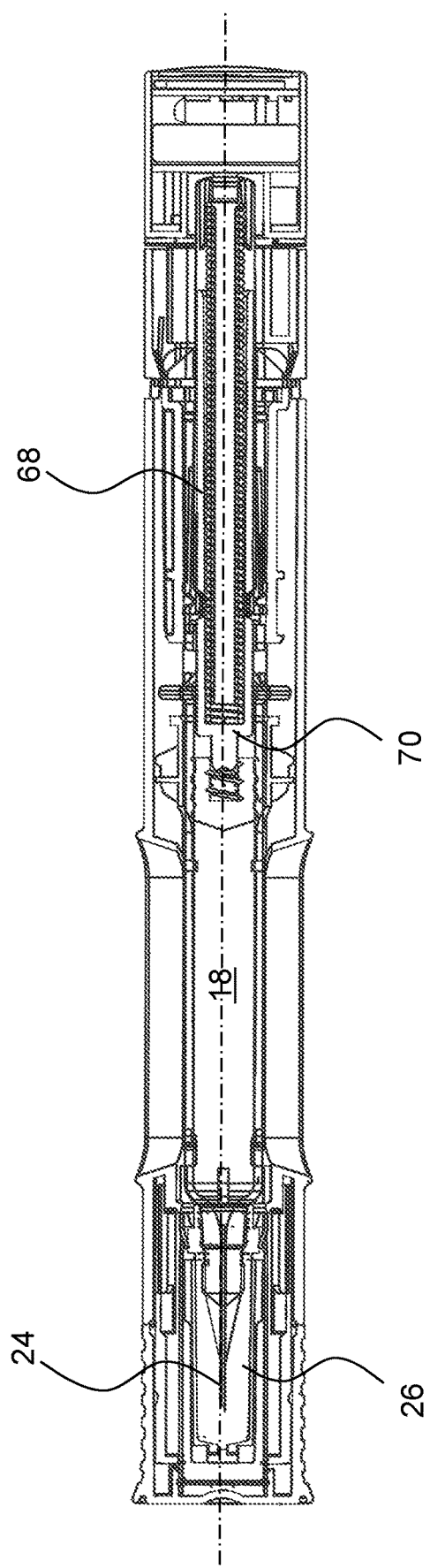
FIG. 2 is a cross-sectional side view of the device of FIG. 1, FIGS. 3, 4 and 8 are detailed views of components comprised in the device of FIG. 1, FIG. 5 comprise exploded views of one feasible identification module according to the disclosure, FIGS. 6 and 7 display mechanical keying element, FIGS. 9 and 10 display electrical keying element, and FIGS. 11 to 15 display detailed views of an electrical keying element and blocking mechanism.

The medicament delivery device shown in the drawings comprises a generally tubular elongated housing 10 having a distal end 12 and a proximal end 14, FIG. 1. The housing 10 is further arranged with windows or openings 16, through which a medicament container 18 can be viewed. The medicament container 18 is arranged with a movable stopper 20. The device further comprises a medicament container holder 22 having a generally tubular shape, FIG. 1. The medicament container holder 22 is arranged to accommodate the medicament container 18, where the medicament container 18 has a proximal end on which a medicament delivery member 24, FIG. 2, is arranged, either made integral or connectable to the medicament container 18. The medicament delivery member 24 is preferably protected before use by a medicament delivery member shield 26 that in the embodiment shown is a so called rigid needle shield or RNS. It is however to be understood that other types of medicament delivery member shields may be used in order to obtain the desired protection of the medicament delivery member 24.

Figure 11:
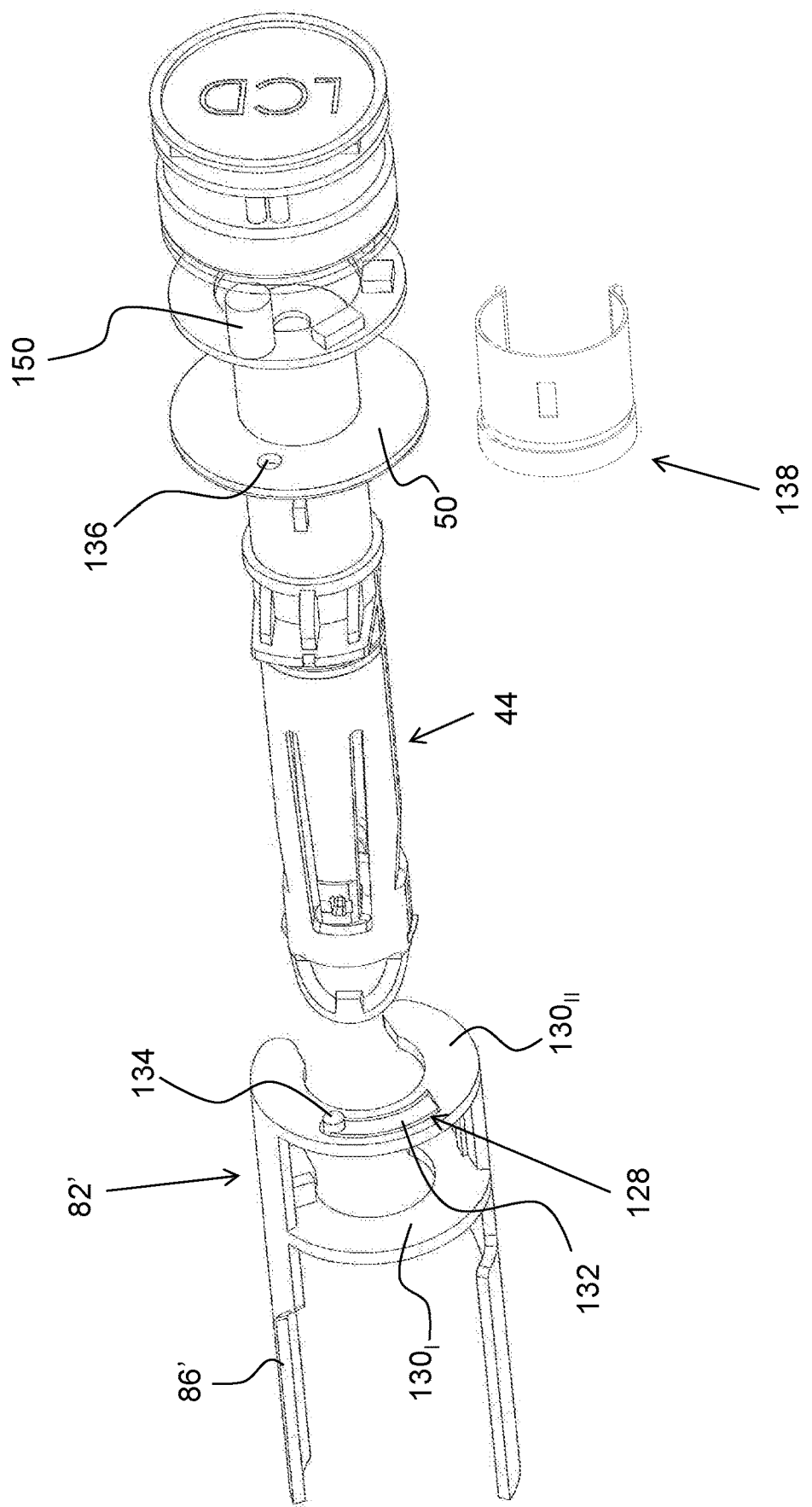
Figure 14:
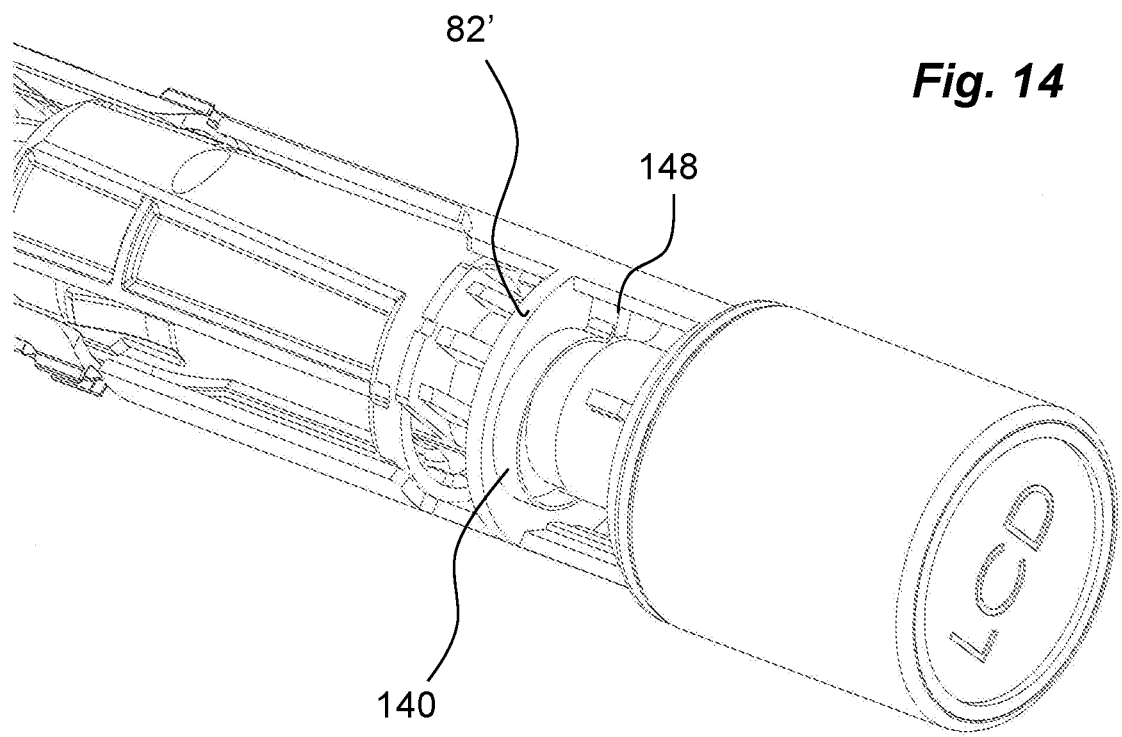

The proximal end of the housing is arranged with a central passage 28, FIG. 1, through which a generally tubular medicament delivery member guard 30 extends, FIGS. 11 and 14. The medicament delivery member guard 30 is in this embodiment an activation mechanism of the medicament delivery device. It is arranged slidable in relation to the housing 10 such that the housing 10 with the medicament container 18 and the medicament delivery member 24 are moved in the proximal direction when the medicament delivery device is pressed against a dose delivery site, thereby exposing the medicament delivery member 24 such that a penetration is performed when the medicament delivery member is an injection needle.

Figure 3:
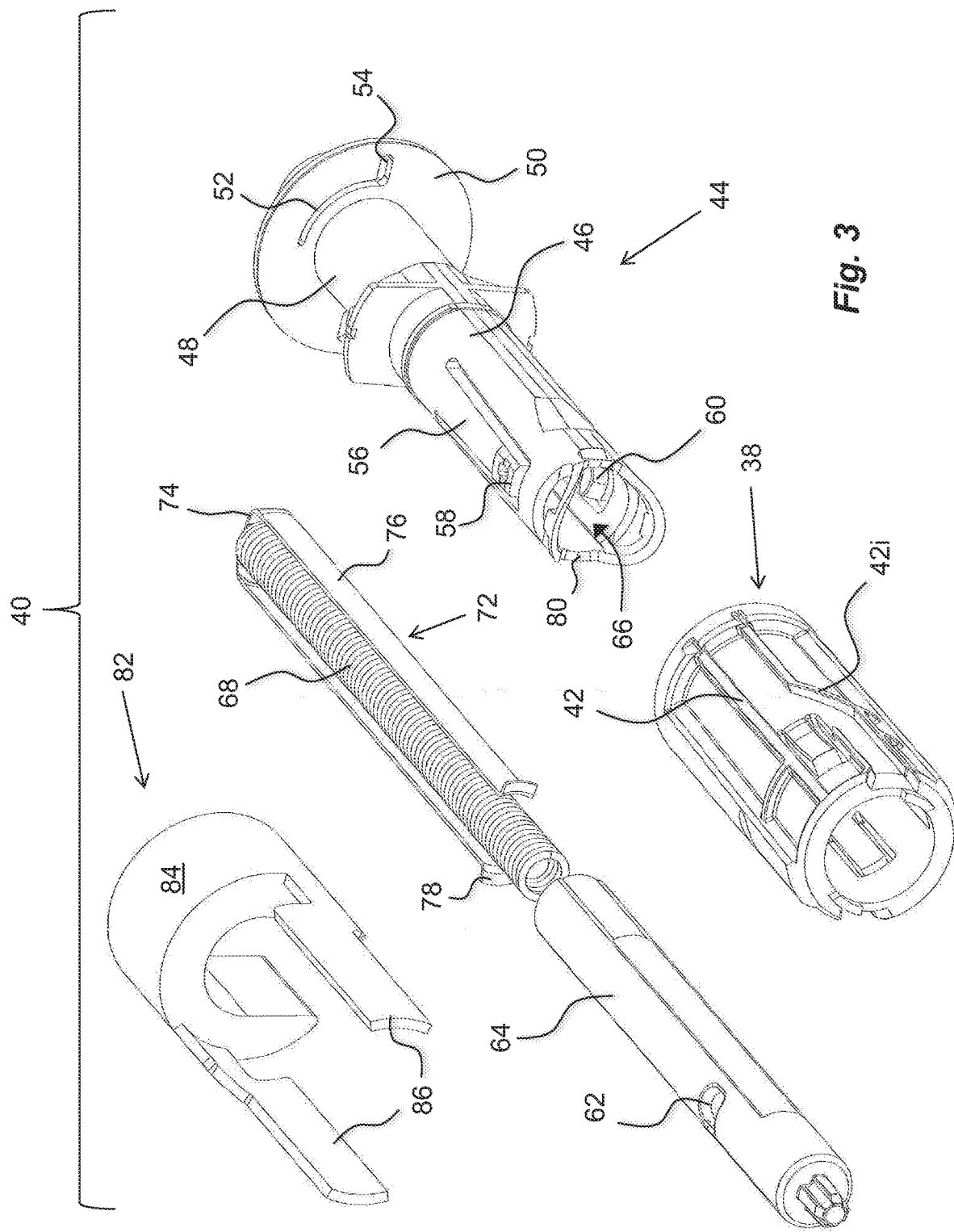

The medicament delivery member shield comprises a proximal tubular part 32 and two distally directed arms 34 extending from the proximal tubular part 32. A medicament delivery member guard spring (not shown) is arranged between a distally directed circumferential wall part of the medicament delivery member guard 30 and a proximally directed circumferential surface of the housing. The arms 34 are arranged slidable along the medicament container holder 22. At the distal end of the arms 34, inwardly directed protrusions 36 are arranged. The protrusions 36 are arranged to operably interact with a rotator 38, FIG. 3, of a drive unit 40, when the delivery member guard is moved in relation to the housing, wherein the rotator 38 is positioned distally of the medicament container 18.

The rotator 38 has a generally tubular shape and is arranged with guide ridges 42 that are intended to cooperate with the protrusions 36 of the medicament delivery member guard 30 as will be described, wherein some sections $42_i$ of the guide ridges are inclined in relation to the longitudinal axis L of the device.

An actuator 44, FIG. 2, is further arranged operably to the rotator 38. It comprises a first proximal tubular section 46 having a diameter slightly smaller than the inner diameter of the rotator 38. It further comprises a generally tubular second section 48 arranged to fit into and to be attached to a distal part of the housing. The second section 48 is provided with a generally circular, radially extending, wall section 50. The wall section 50 is arranged with two grooves 52 shaped as circular arcs placed on opposite sides. At one end of each circular arc a generally radially extending groove 54 is arranged.

The first section 46 is further arranged with proximally extending arms 56 that are arranged flexible in a generally radial direction. The free ends of the arms 56 have outwardly extending protrusions 58 that are to interact with inner surfaces of the rotator 38 as will be described. Further the free ends of the arms 56 are arranged with inwardly extending protrusions 60, which protrusions 60 are intended to interact with recesses 62 on a plunger rod 64. The protrusions 60 extend into a central passage 66 of the actuator 44, in which passage 66 the plunger rod 64 fits.

The drive unit 40 further comprises a compression spring 68 placed inside a cavity of the hollow plunger rod 64, wherein the compression spring 68 is positioned with a proximal end thereof in contact with an end wall 70 of the plunger rod 64, FIG. 2. The distal end of the compression spring 68 is in contact with a generally U-shaped element, hereafter named activator 72, having a base 74 and two arms 76, FIG. 3. The arms 76 of the activator 72 are directed in the proximal direction along, and in contact with, the outer surface of the plunger rod 64, wherein the free ends of the arms 76 are arranged with generally radially outwardly directed ledges 78. These ledges 78 are arranged to be in contact with a proximally directed surface 80 surrounding the central passage 66 of the actuator 44.

As mentioned above, the medicament delivery member guard 30 is moved inside and relative the housing 10 when the medicament delivery device is pressed against a dose delivery site. This in turn causes the protrusions 36 of the medicament delivery member guard 30 to move along the guide ridges 42 of the rotator 38 such that the protrusions will come in contact with the inclined sections $42_i$, which will cause the rotator 38 to turn around the longitudinal axis L of the device.

The turning of the rotator 38 will cause the arms 56 of the actuator 44 to move out of contact with inner surfaces of the rotator 38. The arms 56 of the actuator 44 are now free to flex outwardly, whereby the inwardly directed protrusions 60 of the arms 56 are moved out of contact with the recesses 62 of the plunger rod 64.

The plunger rod 64 is now free to move in the proximal direction due to the force of the compression spring 68, wherein the proximal end of the plunger rod 64 acts on, and moves, the stopper 20 inside the medicament container 18 in the proximal direction such that a dose of medicament is expelled through the medicament delivery member 24.

Figure 4:
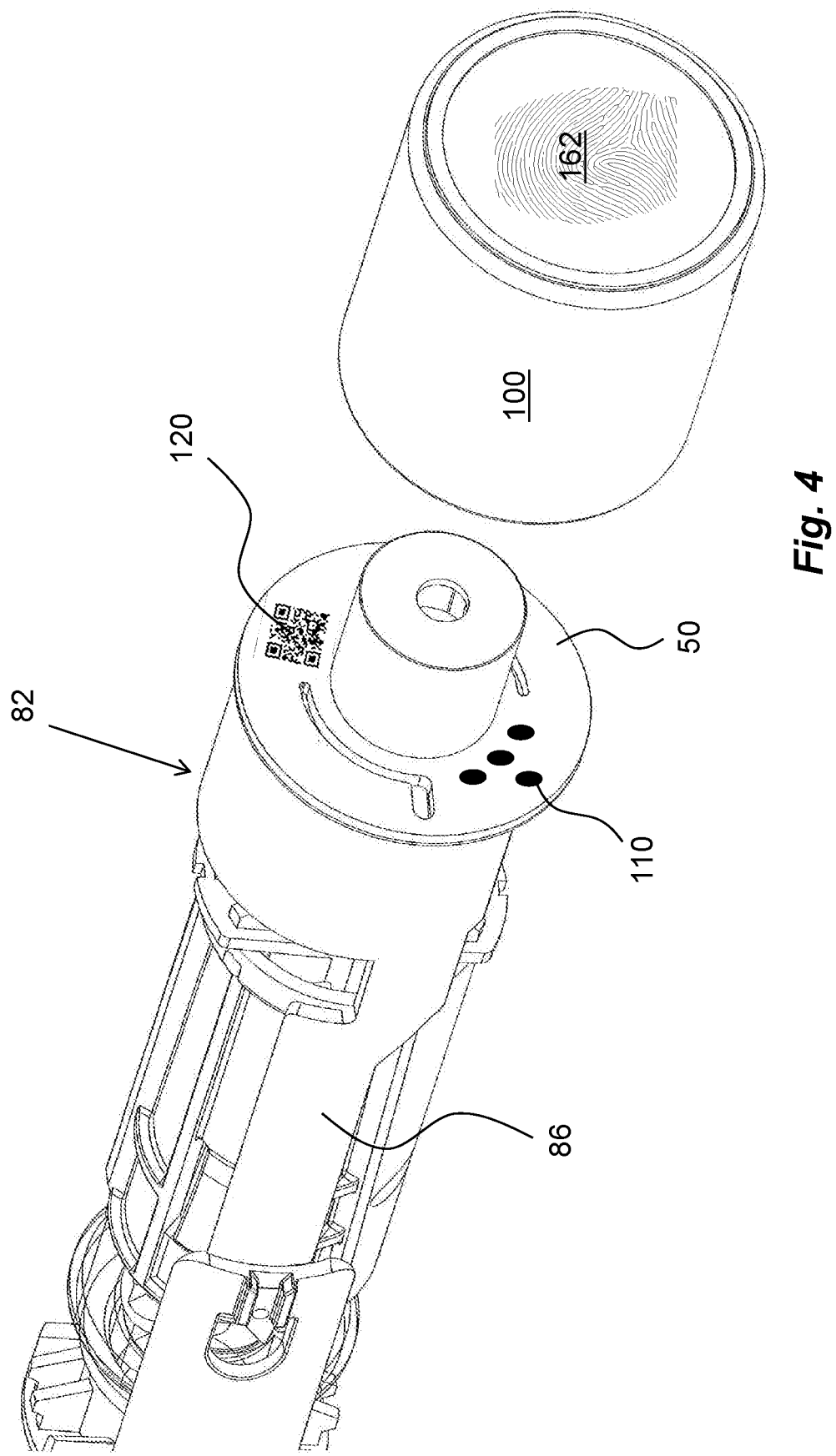

The medicament delivery device is further arranged with an activation preventing mechanism or a locking mechanism which is arranged to prevent use or activation of the medicament delivery device until the locking mechanism is activated. The activation of the locking mechanism may be performed in many ways that will be described below. According to one non-limiting example of a locking mechanism it comprises an activation preventing mechanism that in the embodiments shown is in the form of a blocking element 82, FIG. 3. The blocking element 82 comprises a body 84 that is semi-circular having a central passage that fits around the tubular second section 48 of the actuator 44 such that it may be turned around the second section 48 as will be described. The body 84 of the blocking element 82 further comprises two proximally directed arms 86 positioned radially outside the rotator. As seen in FIG. 4, wherein the device is in a non-activated state, the proximal ends of the arms 86 of the blocking element 82 are in contact with the distal ends of the arms 34 of the medicament delivery member guard 30. Thus, the medicament delivery member guard 30 is locked from being moved in relation to the housing 10 because the arms 34 of the medicament delivery member guard 30 are abutting the arms 86 of the blocking element 82, thereby preventing activation of the device.

In order to activate the medicament delivery device according to the disclosure, the blocking element 82 of the locking mechanism has to be affected such that the medicament delivery member guard 30 can be moved as described above. Further, according to the disclosure, the functions of activation of the medicament delivery device, and thus the deactivation or unlocking of the locking mechanism, should be related and connected to persons authorized and/or approved to use the medicament delivery device, as will be described below.

Identification Module with Keying Features

In that respect, the medicament delivery device according to the present disclosure comprises an identification module 100. According to one aspect of the disclosure, the identification module may be arranged as a separate unit that is attachable to a medicament delivery device. It is however to be understood that the identification module may be an integral part of a medicament delivery device. In the below non-limiting example, the identification module 100 is arranged as a separate unit, as seen in FIG. 2.

The identification module 100 comprises a housing part 102 that is generally tubular, FIG. 5, having generally the same diameter as the housing 10 of the medicament delivery device, as seen in FIG. 2. The identification module 100 is further arranged with keying elements that are arranged and designed to cooperate with corresponding keying elements on the medicament delivery device for unlocking or activating the medicament delivery device so that a dose of medicament may be delivered.

It should be noted that the identification module may have other shapes and designs. For instance, the identification module could be an outer shell that the medicament delivery device is placed in.

Mechanical Keying and Unlocking

Figure 7:
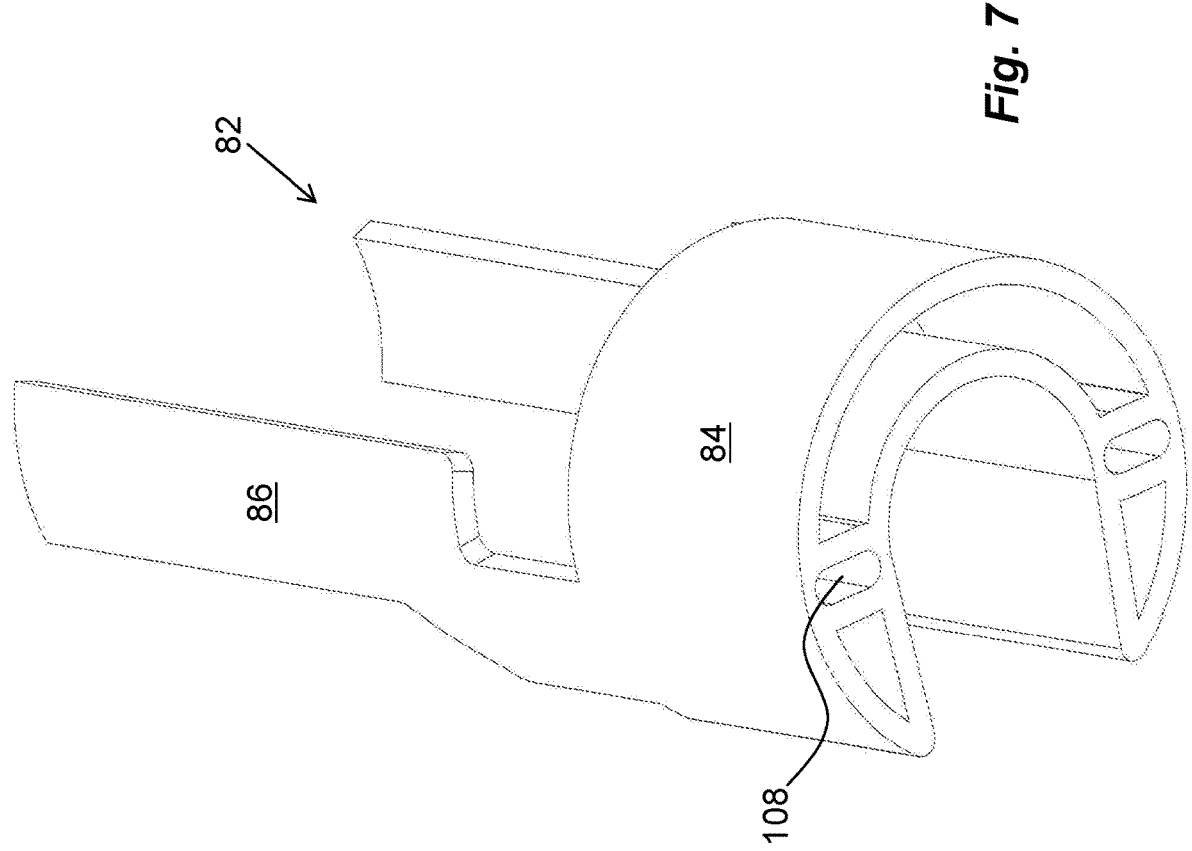
Figure 6:
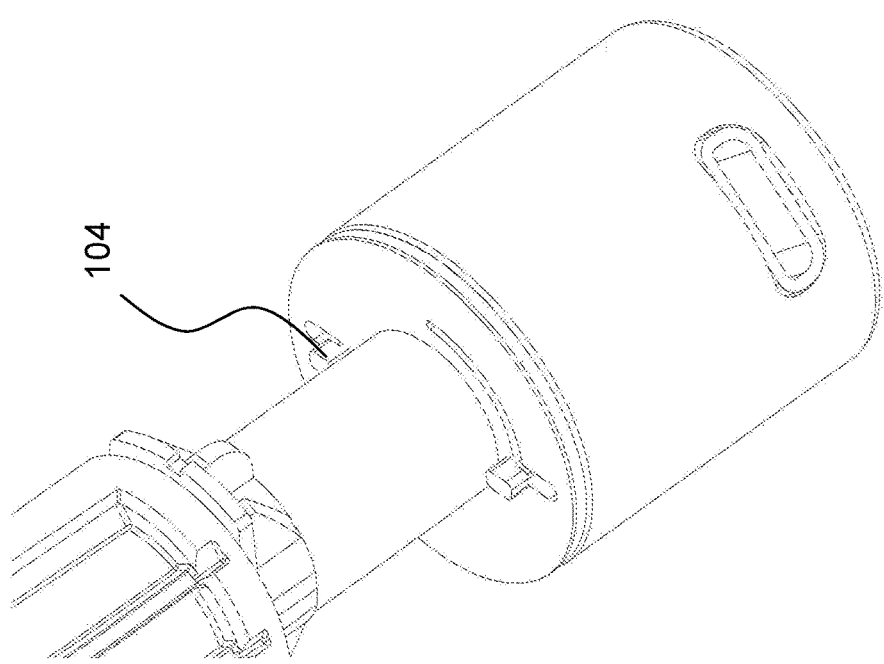

According to one feasible solution, the keying elements are mechanical. As seen in the embodiment according to FIG. 5, the identification module is arranged with keying protrusions 104 mentioned above, which keying protrusions 104 are arranged on a proximally directed surface 106 of the identification module 100. These keying protrusions 104 have a design such as to fit into the radial grooves 54 on the distal end of the medicament delivery device and extend into the grooves 52 of the wall 50 section, FIG. 6. Further, the blocking element 82 is arranged with recesses 108 on its distally directed end surface, FIG. 7, the position of which correspond to the keying protrusions 104 when they are positioned into the radial grooves 54 such that the keying protrusions 104 extend into the recesses 108 of the blocking element 82. When now the identification module 100 is turned around the longitudinal axis L of the medicament delivery device, then the blocking element 82 also is turned. This will in turn move the arms 86 of the blocking element 82 out of contact with the arms 34 of the medicament delivery member guard 30, FIG. 8, whereby the medicament delivery member guard 30 is free to be moved as described above, thereby activating the medicament delivery device to deliver a dose.

It should in this respect be pointed out that a major object of the keying elements is to have a large number of different keying combinations between the identification module and the medicament delivery device in order to "customize" the combinations. Thus if a user has been authorised to receive medicament delivery devices as described above, he or she is given an identification module with a specific key pattern as well as medicament delivery devices with a corresponding key pattern.

Thus, the medicament delivery devices cannot function without the identification modules, and also, identification modules with other key patterns cannot be used. A unique connection is established between the identification module and the medicament delivery devices assigned to the approved user. In this respect, it is to be understood that a large number of mechanical keying elements may be used, such as different number of protrusions, different positions of the protrusions in the radial direction, different cross-section designs of the protrusions and the corresponding recesses or grooves of the medicament delivery device, different positions of the protrusions in the longitudinal direction, different lengths of the protrusions, just to mention a few of the possibilities that the skilled person may design.

Mechanical-Electrical Keying

Another solution of specific key patterns between the medicament delivery device and the identification module could be to use electric contact points 110 on a distally directed surface of the wall section 50 of the medicament delivery device as seen in FIG. 4. The electric contact points 110 could in this regard be placed in relation to each other on other to create a unique pattern. The proximal surface 106 of the identification module 100, intended to be in contact with the distally directed surface of the wall section 50, is arranged with corresponding electric contact points 112, FIG. 5*a*, arranged in the same pattern as the electric contact points 110 of the medicament delivery device such that when the identification module 100 is connected to the medicament delivery device, the contact points 110, 112 are connected to provide electrical contact between the identification module and the medicament delivery device. It should be noted that the patterns may be varied in numerous ways with different positions and/or different number of contact points in order to create "customized" combinations. It is also to be understood that with this solution, either only the contact points are arranged with specific patterns or both the contact points and the mechanical keying elements are arranged with specific patterns. When the electric contact points are used, they can be used to transfer electricity to the medicament delivery device for performing different tasks and functions as will be described.

Electrical Keying

According to another aspect of the disclosure the keying elements may be non-mechanical, e.g. electrical. In that scenario, as seen in FIG. 9 with the housing of the identification module 100 removed, the identification module may comprise a suitable keying circuit 114, suitably powered by an appropriate power source 116 such as a button cell. The keying circuit of the identification module is then capable of connecting and/or communicating with a corresponding keying circuit 118 arranged on the medicament delivery device. In the embodiment shown in FIG. 10, the corresponding keying circuit 118 is placed on the blocking element 82. The connection and/or communication between the keying circuits are then chosen such that a unique "paired" connection is obtained. That is, only a specific identification module may be connectable to specific medicament delivery devices such that the specific medicament delivery devices are unlocked and activated. In this respect it is to be understood that a number of solutions may be provided for activating the device. For instance, NFC-tags may be employed that are programmed with unique combinations. For instance, the keying circuit of the medicament delivery device may contain a passive NFC-tag that is activated by an NFC or RFID reader of the identification module, driven by the power source 116.

Optical Keying

As an alternative, or in addition to the NFC-solution, the keying function may comprise some type of optical keying function comprising an optically identifiable pattern 120, FIG. 4, arranged on the medicament delivery device and some sort of sensor 122, FIG. 5, arranged on the identification module 100 that is capable of identifying the pattern in order to derive information from the pattern. The optically identifiable pattern 120 may in this respect for instance be QR-code, EAN-code or printed letters, placed for instance on a label that is attachable to surfaces of the medicament delivery device, for example as seen in FIG. 4. The identification module is then arranged with suitable optical sensor elements 122 that can read QR- or EAN-code or OCR-read letters. The circuit of the identification module is then arranged with processor and program codes that can identify data from the read information.

Because the pattern is placed on one surface and the sensor is placed on a second surface that are facing each other and that will come in contact with each other when the identification module is attached, it might be quite dark between the pattern and the sensor, making it difficult to read the pattern. The identification module may then be arranged with a light source 124, FIG. 5*a*, that can light up the pattern. In this respect, the light might be chosen outside the visible range and the pattern may be printed with non-visible ink. This may be chosen for making it more difficult to manipulate the keying function.

In order to activate the optical keying function, i.e. the QR-reader and also possibly the lamp, it might be advantageous to have some sort of "power-up" mechanism. In one embodiment, the power-up mechanism may comprise a manually operable switch 126, FIG. 5*b*, arranged on the outer surface of the identification module. When the identification module is to be connected to the medicament delivery device, the user operates the switch, which will cause the power source to be connected to the lamp and/or optical sensor element such that the lamp will illuminate the area in front of the optical sensor element such that the activated optical sensor element will read the pattern. The optical keying function may preferably also comprise a switch-off function that will switch off the power to the optical sensor element and the lamp when the keying operation has been completed, because now the elements of the optical keying function has completed their task.

Regarding the power-up mechanism, it should preferably also comprise a timer function that will switch off the power to the lamp or the optical sensor element after a certain time period if the keying operation is not completed. This will reduce the risk that the power source is depleted if someone activates the power-up mechanism but does not connect the identification module to the medicament delivery device.

It is further understood that the power-up mechanism may activate additional functions as will be described below.

Electrical or Optical Unlocking

Figure 12:
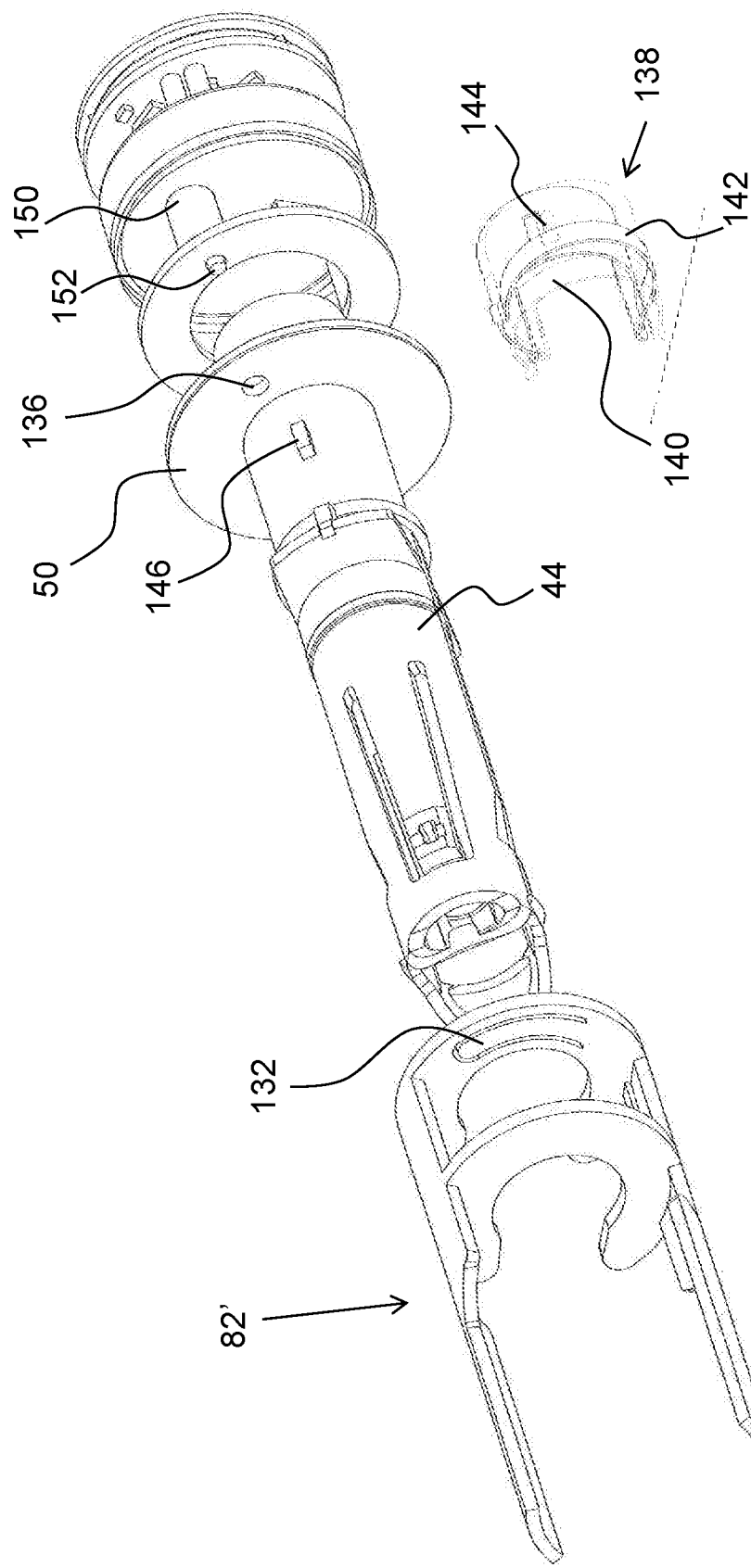
Figure 13:
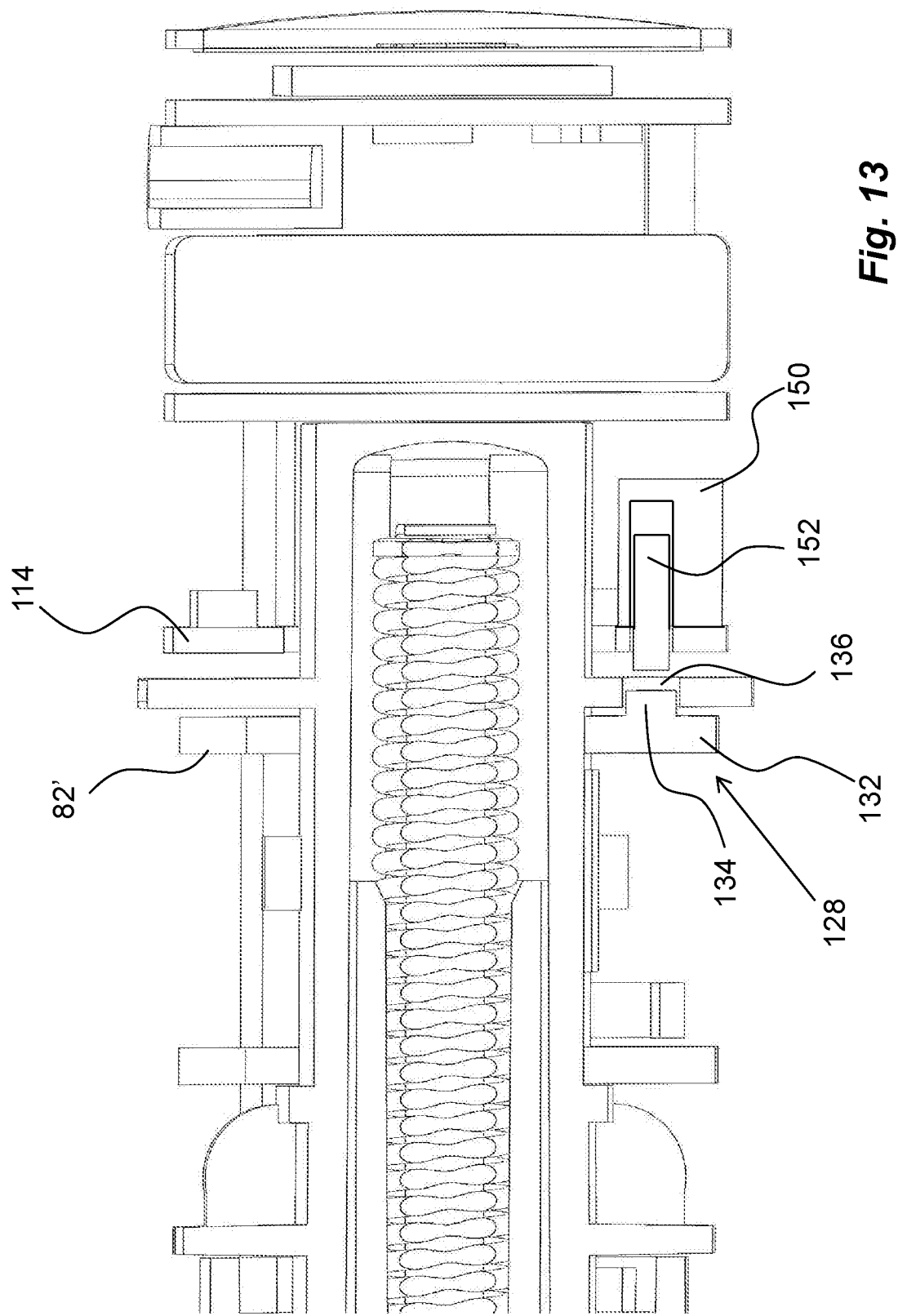

With the electrical or optical keying elements, the keying circuit 118 of the medicament delivery device and/or the identification module may operate a number of different components and/or use a number of different principles in order to unlock and activate the medicament delivery device. For instance, the medicament delivery device is locked by a blocking element 82', FIG. 11, preventing movement of the medicament delivery member guard 30 in relation to the housing 10 as described above, with proximally directed arms 86' preventing movement of the medicament delivery member guard 30. The blocking element 82' could be held in the locking position by a locking element 128. In the embodiment shown in FIG. 11, the blocking element 82' is arranged with two semi-circular discs $130_I$ and $130_{II}$, FIG. 11, oriented transversal to the longitudinal direction L and being adapted to fit around the second section 48 of the actuator 44. The most distally oriented disc $130_{II}$ is arranged with the locking element 128 that in the embodiment shown comprises a flexible arm 132 formed through a generally U-shaped cut-out in the disc $130_{II}$. The free end of the arm 132 is arranged with a distally directed protrusion 134, FIG. 12. The protrusion 134 is arranged and designed to fit into a passage 136 in the wall section 50 of the actuator 44 when the locking element 128 is in the locking position as seen in FIG. 13, whereby the position of the protrusion 134 in the passage 136 prevents any rotational movement of the blocking element 82'. Further, in the initial, locking position, a release element 138 is acting on the blocking element 82' with a force. In the embodiment shown, the release member comprises a torsion spring 140 shaped as an arch and attached to, or made integral with, a seat 142, which seat 142 is arranged to be attached to the second section of the activator. The seat 142 is arranged with a cut-out 144, in which a generally radially extending protrusion 146 on the second section protrudes, in order to lock the release element 138 rotationally. In the initial locked position, the torsion spring 140 is in a tensioned state with its free end resting against a ledge 148 of the blocking element 82' as seen in FIG. 14.

Figure 15:
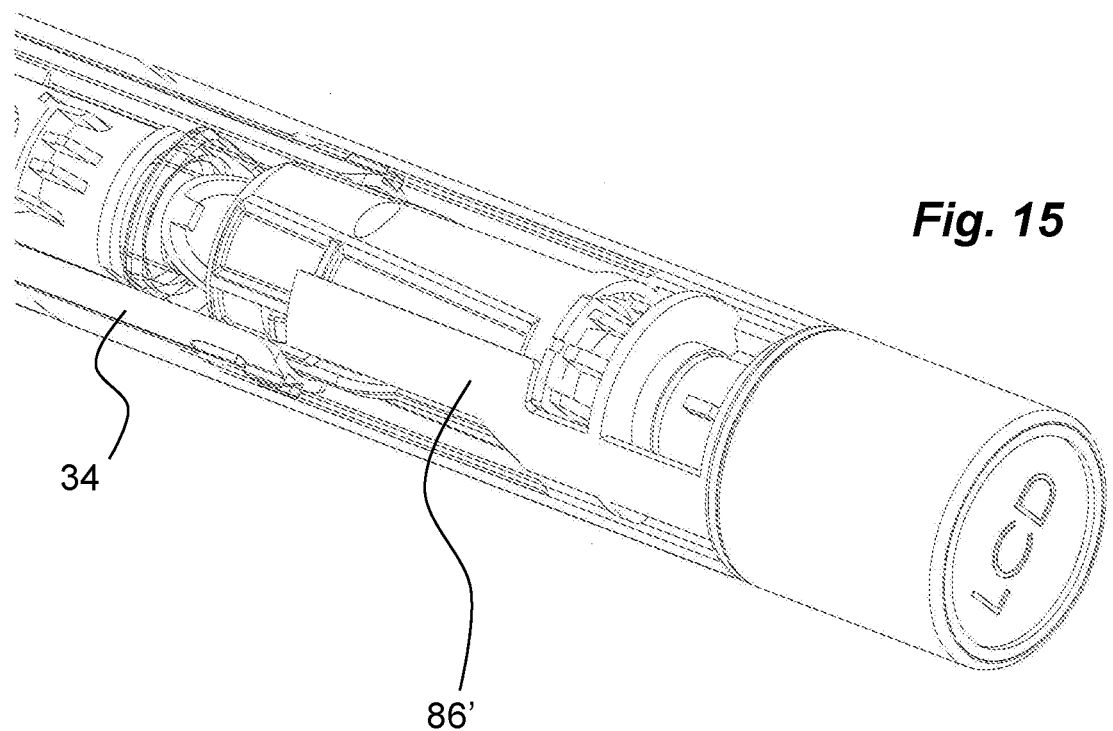

A drive element 150 is operably arranged to act on the locking element when activated. The drive member may be of many designs and functions as will be described below. In the embodiment shown, the drive element 150 is arranged with a rod 152, FIG. 13, or the like elongated member that is movable in the longitudinal direction upon activation. Further, the drive element is operably connected to the keying circuit of the medicament delivery device or to the identification module such that when the identification module is activated, the drive element will act on the locking element 128 such that the blocking element is moved out of a blocking position. In this case the rod 152 of the drive element 150 will push the protrusion 134 of the arm 132 of the locking element 128 out of the passage 136, freeing the blocking element 82'. The torsion spring 140 of the release element 138 is now free to act on and move the arms 86' of the blocking element 82' out of the locking position, FIG. 15. The mechanisms for activating the drive member to move the blocking element will be described below.

The drive member may be designed in a number of ways capable of acting on the blocking element in order to unlock the medicament delivery device. Generally speaking, the drive member may operate by input power in the form of electrical power, by heat or by electromagnetic fields. Of these three principles, some concrete solutions may be mentioned.

The drive member may be operated by electromagnets, wherein the drive member is specifically designed and positioned to be moved by a magnetic field generated by the electromagnets. The electromagnets are in this solution preferably arranged in the identification module especially if the only power source is placed in the identification module.

The drive member may be operated by a solenoid, which solenoid is operated by applying an electric current from the keying circuits. Also here the solenoid is preferably arranged in the identification module. The solenoid is then arranged and designed to act over the interface between the identification module and the medicament delivery device.

The drive member comprises an electro-active polymer which is capable of changing form and/or size when subjected to an electric field. The generator of the electric field is then preferably arranged in the identification module and operated by the keying circuit of the identification module.

The drive member comprises a bimetallic strip. The two metallic parts have different thermal expansion properties. The identification module is arranged with heating element that upon activation will heat the bimetallic strip such that it will change position.

The drive member comprises a permanent magnet creating a magnetic field that holds the blocking member in the locking position. The identification module is arranged with a heating element that upon activation will heat the permanent magnet to a temperature above the curie point of the material of the permanent magnet. The permanent magnet will then lose its magnetic properties whereby the blocking member is released.

The drive member comprises a shape memory alloy or a shape memory polymer. The identification module is arranged with a heating element that upon activation will heat the shape memory material such that it will retain its original shape upon applying heat to the material.

The drive member comprises a magnetic memory alloy. The identification module is arranged with a generator of magnet field that upon activation will affect the magnetic memory alloy such that it will change its position.

In the above examples of preventing activation or blocking of the medicament delivery device, a medicament delivery member guard is blocked until activation. It is however to be understood that other activation mechanisms and thus elements of the medicament delivery device may be blocked, depending on the actual design of the device. For instance, an activation button may be blocked, a drive unit, such as a piston rod may be blocked, activation components are positioned out of contact with each other until the keying is confirmed and the components are moved in contact with each other, thereby enabling activation of the medicament delivery device.

In order to operate the optical or electrical keying and unlocking functions, a power source is needed. The power source is preferably arranged in the identification module only. There are a number of reasons for this. One reason is that the identification module may be arranged with a number of additional functions, apart from the keying function, that may require power, which additional functions will be described below. Another reason is that the medicament delivery device may be a so called disposable device that is to be discarded after use. It would then be a drawback if there was a power source inside the medicament delivery device that would also be discarded, especially if the power source was a battery possibly containing environmentally hazardous chemical elements. A further reason is to reduce the manufacturing costs by not having any power sources in the medicament delivery device. However, in spite of the reasons stated above, there might be occasions and design aspects that will require or justify a power source also in the medicament delivery device.

There are further features that the identification module may comprise and other function that it may perform. As seen in FIGS. 5 and 9, the identification module 100 comprises a circuit 154 in turn comprising processors and storage elements. The processors may be designed and programmed to perform a number of different tasks as will be described. The circuit 154 of the identification module may further comprise communication circuits both internal with elements of the medicament delivery device as well as external with adjacently positioned elements and remotely positioned elements. Further, the identification module may comprise input/output elements such as contacts 156 and buttons 158 operably connected to the circuit 154, FIG. 5a.

The circuit 154 of the identification module may further comprise a user communication circuit that is arranged and programmed to communicate with a user. The user communication circuit may comprise display elements that can communicate visually, e.g. by text stored in the electronics module that is displayed on a suitable display 160 on the device, FIG. 9. In addition to, or instead, the user communication circuit may comprise audio elements that can communicate audibly, e.g. by a recorded message stored in the electronics module that is played in an appropriate loudspeaker of the electronics module or of the device as such.

Identification

According to the disclosure, the identification module 100 could also comprise an identification mechanism that is capable of identifying a specific person or specific persons that are assigned and allowed to use the medicament delivery device. The identification mechanism may comprise different features and functions. For instance, the identification module may be arranged with a number of buttons 158, as mentioned above, or the like activators and in order to activate the medicament delivery device, a certain combination of buttons have to be contacted, like a pin code. The entered code is compared to a pre-stored code in the identification module and if there is a correct match, then the medicament delivery device is unlocked as described above.

Instead of, or in addition to, buttons, the identification module may comprise a reading sensor 162, FIG. 4. This reading sensor 162 may be capable of collecting biometrical data from a user. For instance the reading sensor may be designed to read fingerprints, and when a user is to activate the medicament delivery device, he/she places a finger on the sensor, or swipes the finger over the sensor, whereby the fingerprint is read. The identification module then compares the read fingerprint with pre-stored fingerprints from the user, and if there is a match, the medicament delivery device is unlocked. Instead fingerprints, the reading sensor may be designed to read the iris of a person and compare the readings with a pre-stored reading of the proper user's iris. If there is a match, then the medicament delivery device is unlocked as described above.

Local Communication

One feasible communication capability is a local communication with different sensors and circuits arranged in the medicament delivery device. If the identification module is an integral part of the medicament delivery device, then suitable circuitry may be arranged inside the housing such as wiring or Laser Direct Structuring (LDS). On the other hand, if the identification module is arranged as a separate attachable unit, then an appropriate signal transferring interface has to be created. In one solution, the interface may comprise electric contact points on opposing surfaces that are brought in contact with each other when the identification module is attached to the medicament delivery device. As a further solution, the signal transferring interface may comprise elements that provide wireless communication between the electronics of the identification module and the different sensor elements of the medicament delivery device. Since they are positioned very close to each other, radio frequency identification technology may be used and in particular NFC technology may be used as mentioned above in connection with keying. The identification module is then preferably arranged with an NFC-tag comprising an NFC-chip, circuitry, memory elements and an antenna. The different sensor elements of the medicament delivery device may then also be arranged with NFC-tag, enabling communication between the NFC-tag of the identification module and the medicament delivery device.

There are a number of features that could be utilized in the local mode. These are among others positioning an NFC-tag on the medicament container. This could either be done by a label attached to the outer surface of the medicament container. Another solution is to embed the NFC-tag in the material of the medicament container when manufactured. Placing an NFC-tag in contact with the medicament container enables a number of features. Data regarding the drug contained in the medicament container could be derived. The data retrievable could for example be size of the medicament container, the type of drug, strength of the drug, date of filling, this data could be transmitted to the identification module and stored. The transmitted data could further be compared to user-specific data pre-stored in the identification module such as prescribed medicament, drug strength etc.

Further, since the NFC-tags generally have integrated temperature sensors, it is possible to measure the temperature of the medicament container. For many drugs, they should be stored in cool places like refrigerates in order to maintain the life of the drug. However, when the drug is to be administered, it should have generally room temperature. The NFC-tag of the medicament container may then be able to monitor the temperature and transmit this to the identification module. The identification module is then programmed such that the medicament delivery device cannot be activated until the identification module receives data from the NFC-tag of the medicament container that the temperature is above a threshold temperature. Then the identification module may activate and unlock the medicament delivery device such that it may be used for administering a dose of medicament.

The temperature feature of the NFC-tag may further be used for providing a temperature log in that the identification module may sample temperature data and time stamp the data. The temperature log may then be used for controlling that the drug of the medicament container has not been exposed to excessive temperatures that may have damaged or degraded the drug. The device may further be arranged with sensors that are capable of sensing the end of a dose delivery sequence and to provide a signal to the identification module. The latter may combine this signal with a time stamp in order to provide information when the drug has been taken by the user. The information may also be provided to a user handling a number of devices for alerting that the particular device has been already used and should be discarded.

Further, the medicament delivery device may be arranged with sensors that are capable of obtaining information that a medicament delivery device has been tampered with. For instance, the medicament delivery device may be arranged with a protective cap that will keep medicament delivery members sterile, which protective cap has to be removed before use. Sensors may then be arranged to identify that the protective cap has been removed earlier, and being put back again, which has adversely affected the sterility of the medicament delivery member. This information is transmitted to the identification module, which will not activate the medicament delivery device if the user should try to do so. In the above scenarios, the user communication unit may be activated for informing the user why the device is not activated so that the user may understand and take appropriate measures for obtaining a functional medicament delivery device.

Global Communication

Preferably the circuit 154 of the identification module 100 may also comprise a communication circuit that is capable of communicating with external communication networks such as among others digital cellular networks such as mobile telephone networks, GSM, 3G, 4G, etc. as well as WLans, just to mention a few that are very familiar to a skilled person in the art of wireless communication. The communication with external communication networks may provide further identification possibilities as well as exchange of information to and from the medicament delivery device and the identification module.

For example, when the identification module is connected to databases in the external communication networks, the earlier mentioned data regarding the medicament can be directly checked and verified. For instance, the drug information obtained, such as type of drug and manufacturing date may be compared to a dedicated database available via the communication network. The comparison may then be done regarding the connection user and prescribed drug. If the comparison does not match then the medicament delivery device may not be activated. Also, the date of manufacturing of the drug in the medicament delivery device may be compared to information regarding the specific drug. For instance, a certain batch of the drug may have been recalled for different reasons. When the identification module receives such information, it might prevent the medicament delivery device from being unlocked. Also, there might be a set time limit when the drug is valid to take, i.e. an expiry date. After the expiry date, the device may be prevented from being unlocked by the information received by the identification module.

The identification data described above in connection with pin codes and biometrical sensors may be stored in external databases rather than locally in the identification module. When now a pin code has been entered or a reading sensor has read a fingerprint or an iris, the communication unit of the identification module contacts the database that contains pre-stored data regarding the correct pin-codes or the specific patterns of the fingerprint or iris of a certain user. The match is then done externally and if there is a match, approval signals are transmitted to the identification module, whereby the medicament delivery device is unlocked.

Further, user data that may be stored externally are patient prescriptions, patient treatment schemes as well as payment authentication. Regarding patient prescriptions, the identification module may retrieve information that a prescription is about to end or expire and/or that a prescription has been renewed and that the user may go to the pharmacist for collecting new medicament delivery devices. This information retrieved by the identification module may be communicated to the user via the user communication circuit of the identification module, visually and/or audibly.

Further, the identification module may retrieve information regarding the treatment schemes that a physicist has put together for a certain drug and a certain patient. Regarding the treatment scheme, this may be compared to the actual drug delivery actions performed by the user, which actions have been monitored by the identification module in communication with the sensors of the medicament delivery device, wherein the identification module has time stamped the actions. Also here, the information retrieved by the identification module may be communicated to the user via the user communication circuit, and in particular if the user has deviated from the prescribed treatment scheme. The user may in that respect also be informed what measures that need to be taken in order to remedy the deviation.

Payment authentication may be used if for example the prescribed drug has to be paid partly by the user or the insurance company of the user. The external database may then be arranged to check and/or to receive information regarding the payment of the drug. This information may then be transmitted to the identification module for further actions. One action may be to inform or alert the user that a payment needs to be performed via the user communication circuit. Another action is to block the medicament delivery device until a payment has been performed.

User Interaction with Other Device

For some types of treatment, it is important that the condition of the patient/user is monitored regularly, for instance to see that the patient adhere to the prescribed treatment or to monitor the progress of a treatment scheme. In doing so, different types of measurement sensors and measurement devices may be utilized. Regarding diabetes for instance, it is quite common to monitor the blood sugar level and a number of measurement devices provided with blood sugar level sensors have been and are being developed. According to the disclosure, the communication unit of the medicament delivery device may communicate with such a measurement device. The identification module may then be designed such that the medicament delivery device remains locked until the measured values are outside permissible values, indicating that a dose of medicament needs to be administered. The identification module then unlocks the device.

Further, the user communication circuit may alert the user that a dose needs to be taken and that the medicament delivery device is unlocked. The information regarding the monitoring and possibly the alerting of the user, together with a time stamp, may be transmitted by the identification module to external databases. This information may then be analysed by physicians or other trained staff for e.g. evaluating the progress of a treatment or testing response of clinical trials.

Regarding communication with other devices, this function may be utilized in combination with smart devices as defined above. For instance, when the identification module is arranged with a communication circuit, it may communicate directly with a smart device, wherein the communication system could be near range communication such as Bluetooth, ZigBee, Ant or the like, it could be via telecommunication networks such as GSM, 4G, 5G, or it could be via Wlan etc.; in short any suitable wireless communication network.

The smart device could be used for identifying the person authorised to use and/or to activate the medicament delivery device. The authorised person could be the patient or an approved person that will assist the patient, such as a parent or trained healthcare staff. Different functions of the smart device could then be used for activating the medicament delivery device via data transmitted from the smart device to the identification module. For instance, the smart device could require that a certain pin code be entered by the authorised user. Another solution is to use biometric data such as e.g. fingerprints, eyes or faces, etc. if the smart device is arranged to be able to read such data and compare it with stored data. A further scenario could be to use authorised identification functions such as Bank-ID or the like.

A further scenario is that an authorised person such as a physician provides data to the smart device in real time via e.g. a home page or an application accessible via the smart device. The physician may also, or instead, activate the medicament delivery device directly via the networks, upon receiving information that the authorised person is handling the medicament delivery device, which information is transmitted via the smart device. In that respect, a picture or a video sequence may be sent to the physicist. Also, applications like Face Time may be used.

Interaction with Other Authorised Person or Persons

The treatment of patients may require regular monitoring and interaction from authorized persons such as physicians. For some drugs that are very potent and/or very expensive and/or require that they are taken only on specific approval of an authorized person, for example after evaluating the progress of a certain treatment as described above, the medicament delivery devices may only be unlocked by the user in cooperation with the authorised person, or may only be unlocked by the authorised person. In this case, the authorised person may transmit an approval signal to the identification module after he/she has studied data from the treatment. This will unlock the medicament delivery device, either directly or in combination with identification of the user, where the latter scenario is preferable since a double safety aspect is gained. As mentioned before, the user communication circuit may be activated when the authorised person has approved the administration of the drug in order to alert the user that the medicament delivery device may be used for administering a dose.

Sequence Dependence with Other Drugs or Other Events

The unlocking of the medicament delivery device according to the disclosure may be based on further criteria and operations. For instance, a patient may use several drugs, which drugs may or may not be combined with each other, and/or should be taken at different intervals and/or with certain time delay between them. Information regarding date and time of dose delivery of one drug may be transmitted from the identification module to an external database. The database then has information when a different drug may be administered and will not permit unlocking of a medicament delivery device containing the different drug until a prescribed time interval has lapsed. As mentioned before, the user may be alerted or informed regarding the actions via the user communication circuits.

A number of different identification measures and a number of different actions have been described above. It should be understood that these measures and these actions may be combined in many ways in order to obtain the desired level of safety and security against wrong person handling the medicament delivery device, or wrong handling of the medicament delivery device by rightful user.

It is to be understood that the embodiments described above and shown in the drawings are to be regarded only as non-limiting examples of the disclosure and that it may be modified in many ways within the scope of the patent claims.

The invention claimed is:

1. A medicament delivery device comprising:
   a housing, which housing is arranged to accommodate a medicament container,
   a drive unit operably arranged to act on the medicament container upon activation,
   a delivery member guard slidably positioned in the housing,
   an activation mechanism operably arranged to be operated by a user,
   an activation preventing mechanism comprising a rotatable blocking element that engages the delivery member guard to prevent distal axial moment of the delivery member guard when the activation prevention mechanism is in a locking position to prevent the activation mechanism from being activated,
   an identification module arranged to be operated by the user, which identification module is designed as an attachable unit to the medicament delivery device,
   mechanical keying elements arranged on the medicament delivery device and on said identification module designed to interact with each other when physically attaching said identification module to the medicament delivery device, where the physical attachment of the identification module to the medicament delivery device causes the activation prevention mechanism to unlock, and
   first electrical keying elements comprised in said identification module, wherein the first electrical keying elements are capable of obtaining identification information, such that the identification information obtained is compared to stored data and authenticated by the identification module, and wherein the authentication allows the blocking element to rotate relative to the housing so that the delivery member guard is free to move distally relative to the housing such that the activation mechanism can then be activated.

2. The medicament delivery device according to claim 1, wherein the stored data is stored in the identification module.

3. The medicament delivery device according to claim 1, wherein the medicament delivery device comprises second keying elements containing identification information and wherein said identification module is arranged to obtain the identification information from said second keying elements of said medicament delivery device.

4. The medicament delivery device according to claim 1, wherein the identification module further is provided with circuits that communicate with external communication elements.

5. The medicament delivery device according to claim 4, wherein said circuits comprise near range communication technology.

6. The medicament delivery device according to claim 4, wherein said circuits comprise wireless local area network communication technology.

7. The medicament delivery device according to claim 6, wherein said circuits comprise digital cellular network communication technology.

8. The medicament delivery device according to claim 4, wherein the stored data is derived from external information sources.

9. The medicament delivery device according to claim 4, wherein said circuits in the identification module are configured to communicate with communication elements located within the housing, the drive unit, the activation mechanism, or the activation prevention mechanism of the medicament delivery device.

10. The medicament delivery device according to claim 4, wherein said identification module is arranged with a GPS circuit capable of obtaining information regarding an actual position of an activated medicament delivery device and wherein said circuits are designed to transmit position information.

11. The medicament delivery device according to claim 1, wherein the identification information pertains to identification of the user.

12. The medicament delivery device according to claim 1, wherein the identification information pertains to usage of the medicament delivery device.

13. The medicament delivery device according to claim 1, wherein deactivation is performed by electrical power, magnetic fields, or heat generated by the identification module.

14. The medicament delivery device according to claim 1, wherein said identification module comprises electrical input elements that allow the user to input identifying information into the identification module.

15. The medicament delivery device according to claim 14, wherein said electrical input elements comprise buttons to allow input of a specific code.

16. The medicament delivery device according to claim 14, wherein said electrical input elements comprise biometrical sensors.

17. A medicament delivery device comprising:
a housing configured to hold a medicament container;
a drive unit operably arranged to act on the medicament container upon activation of the drive unit;
an activation mechanism configured for operation by a user;
a delivery member guard slidably positioned in the housing:
an activation preventing mechanism comprising a rotatable blocking element that engages the delivery member guard to prevent distal axial moment of the delivery member guard when the activation prevention mechanism is in a locking position to prevent the activation mechanism from being activated;
an identification module operably by the user, which identification module is designed as an attachable unit to the medicament delivery device; and
mechanical keying elements arranged on the medicament delivery device and on said identification module designed to interact with each other when physically attaching said identification module to the medicament delivery device, where the physical attachment of the identification module to the medicament delivery device causes the activation prevention mechanism to unlock;
wherein the identification module further comprises first electrical keying elements that are capable of obtaining identification information, such that the identification information obtained is compared to stored data and authenticated by the identification module,
wherein the authentication allows the blocking element to rotate relative to the housing so that the delivery member guard is free to move distally relative to the housing such that the activation mechanism can then be activated to allow operation of the activation mechanism and deactivation is performed by electrical power, magnetic fields, or heat generated by the identification module,
wherein the medicament delivery device further comprises second keying elements containing the identification information, and
wherein said identification module is arranged to obtain the identification information from said second keying elements.

18. The medicament delivery device of claim 17 where the activation preventing mechanism is a blocking element and that the deactivation by the identification module will cause the blocking element to be moved to a non-blocking position.

19. The medicament delivery device according to claim 17 where the identification module further comprises electrical input elements that comprise biometrical sensors.

* * * * *